(12) United States Patent
Lawson

(10) Patent No.: US 12,114,894 B1
(45) Date of Patent: Oct. 15, 2024

(54) FOOT-EXFOLIATING DEVICE

(71) Applicant: Bolaji Lawson, Cumming, GA (US)

(72) Inventor: Bolaji Lawson, Cumming, GA (US)

(*) Notice: Subject to any disclaimer, the term of this patent is extended or adjusted under 35 U.S.C. 154(b) by 231 days.

(21) Appl. No.: 17/857,479

(22) Filed: Jul. 5, 2022

(51) Int. Cl.
*A61B 17/54* (2006.01)
*A47K 7/02* (2006.01)

(52) U.S. Cl.
CPC .............. *A61B 17/54* (2013.01); *A47K 7/026* (2013.01)

(58) Field of Classification Search
CPC ................................ A47K 7/026; A61B 17/54
USPC ....................................................... 4/606, 622
See application file for complete search history.

(56) References Cited

U.S. PATENT DOCUMENTS

| | | | |
|---|---|---|---|
| 2,852,793 A * | 9/1958 | Shelton | A47K 7/026 15/159.1 |
| 4,617,917 A | 10/1986 | Miller | |
| 5,321,867 A | 6/1994 | Probst | |
| 5,473,788 A * | 12/1995 | Aragona | A47K 7/026 15/244.4 |
| 5,729,858 A | 3/1998 | Riffel | |
| 5,758,381 A * | 6/1998 | Rocha | A47K 7/026 4/606 |
| 5,913,313 A * | 6/1999 | Brunderman | A61B 17/54 132/200 |
| 10,376,107 B1 | 8/2019 | Reneau | |
| 10,716,595 B1* | 7/2020 | Situ | A61B 17/54 |
| 2008/0235892 A1* | 10/2008 | Williams | A47K 7/026 4/606 |
| 2009/0159092 A1 | 6/2009 | Munoz | |
| 2020/0222083 A1 | 7/2020 | Fritz | |
| 2020/0345184 A1 | 11/2020 | Carter | |

FOREIGN PATENT DOCUMENTS

WO 2006121392 11/2006

* cited by examiner

*Primary Examiner* — Tuan N Nguyen
(74) *Attorney, Agent, or Firm* — Kyle A. Fletcher, Esq.

(57) ABSTRACT

The foot-exfoliating device may be adapted for a user to exfoliate a user's foot while the user is in a shower. The foot-exfoliating device may be mounted in a bottom corner of the shower where a floor meets a wall. The foot-exfoliating device may be adapted to exfoliate the user's foot when the user's foot is placed on a curved top surface with a heel of the user's foot pressed into a heel well and when a sole of the user's foot is dragged along a plurality of foot scrubbers that may be accessible on the curved top surface. The foot-exfoliating device may comprise a scrubber body and a mounting base. The scrubber body may be operable to exfoliate. The mounting base may couple the scrubber body to the shower.

16 Claims, 4 Drawing Sheets

FOOT-EXFOLIATING DEVICE

CROSS REFERENCES TO RELATED APPLICATIONS

Not Applicable

STATEMENT REGARDING FEDERALLY SPONSORED RESEARCH

Not Applicable REFERENCE TO APPENDIX
Not Applicable

BACKGROUND OF THE INVENTION

Field of the Invention

The present invention relates to the fields of personal grooming and skin care, more specifically, a foot-exfoliating device.

SUMMARY OF INVENTION

The foot-exfoliating device may be adapted for a user to exfoliate a user's foot while the user is in a shower. The foot-exfoliating device may be mounted in a bottom corner of the shower where a floor meets a wall. The foot-exfoliating device may be adapted to exfoliate the user's foot when the user's foot is placed on a curved top surface with a heel of the user's foot pressed into a heel well and when a sole of the user's foot is dragged along a plurality of foot scrubbers that may be accessible on the curved top surface. The foot-exfoliating device may comprise a scrubber body and a mounting base. The scrubber body may be operable to exfoliate. The mounting base may couple the scrubber body to the shower.

An object of the invention is to provide a foot-exfoliating device that may be mounted in a shower at a bottom corner of the shower.

Another object of the invention is to provide a heel well comprising a heel well abrasive surface such that the heel well abrasive surface may exfoliate the heel when the heel is moved within the heel well.

A further object of the invention is to provide a plurality of foot scrubbers comprising scrubber abrasive surfaces such that the scrubber abrasive surfaces may exfoliate the sole when the sole is moved over and around the plurality of scrubbers. Yet another object of the invention is to provide a mount that may couple the body of the foot-exfoliating device to the wall of the shower using an adhesive.

These together with additional objects, features and advantages of the foot-exfoliating device will be readily apparent to those of ordinary skill in the art upon reading the following detailed description of the presently preferred, but nonetheless illustrative, embodiments when taken in conjunction with the accompanying drawings.

In this respect, before explaining the current embodiments of the foot-exfoliating device in detail, it is to be understood that the foot-exfoliating device is not limited in its applications to the details of construction and arrangements of the components set forth in the following description or illustration. Those skilled in the art will appreciate that the concept of this disclosure may be readily utilized as a basis for the design of other structures, methods, and systems for carrying out the several purposes of the foot-exfoliating device.

It is therefore important that the claims be regarded as including such equivalent construction insofar as they do not depart from the spirit and scope of the foot-exfoliating device. It is also to be understood that the phraseology and terminology employed herein are for purposes of description and should not be regarded as limiting.

BRIEF DESCRIPTION OF DRAWINGS

The accompanying drawings, which are included to provide a further understanding of the invention are incorporated in and constitute a part of this specification, illustrate an embodiment of the invention and together with the description serve to explain the principles of the invention. They are meant to be exemplary illustrations provided to enable persons skilled in the art to practice the disclosure and are not intended to limit the scope of the appended claims.

DETAILED DESCRIPTION OF THE EMBODIMENT

The following detailed description is merely exemplary in nature and is not intended to limit the described embodiments of the application and uses of the described embodiments. As used herein, the word "exemplary" or "illustrative" means "serving as an example, instance, or illustration." Any implementation described herein as "exemplary" or "illustrative" is not necessarily to be construed as preferred or advantageous over other implementations. All of the implementations described below are exemplary implementations provided to enable persons skilled in the art to practice the disclosure and are not intended to limit the scope of the appended claims. Furthermore, there is no intention to be bound by any expressed or implied theory presented in the preceding technical field, background, brief summary or the following detailed description. As used herein, the word "or" is intended to be inclusive.

Figure 1:
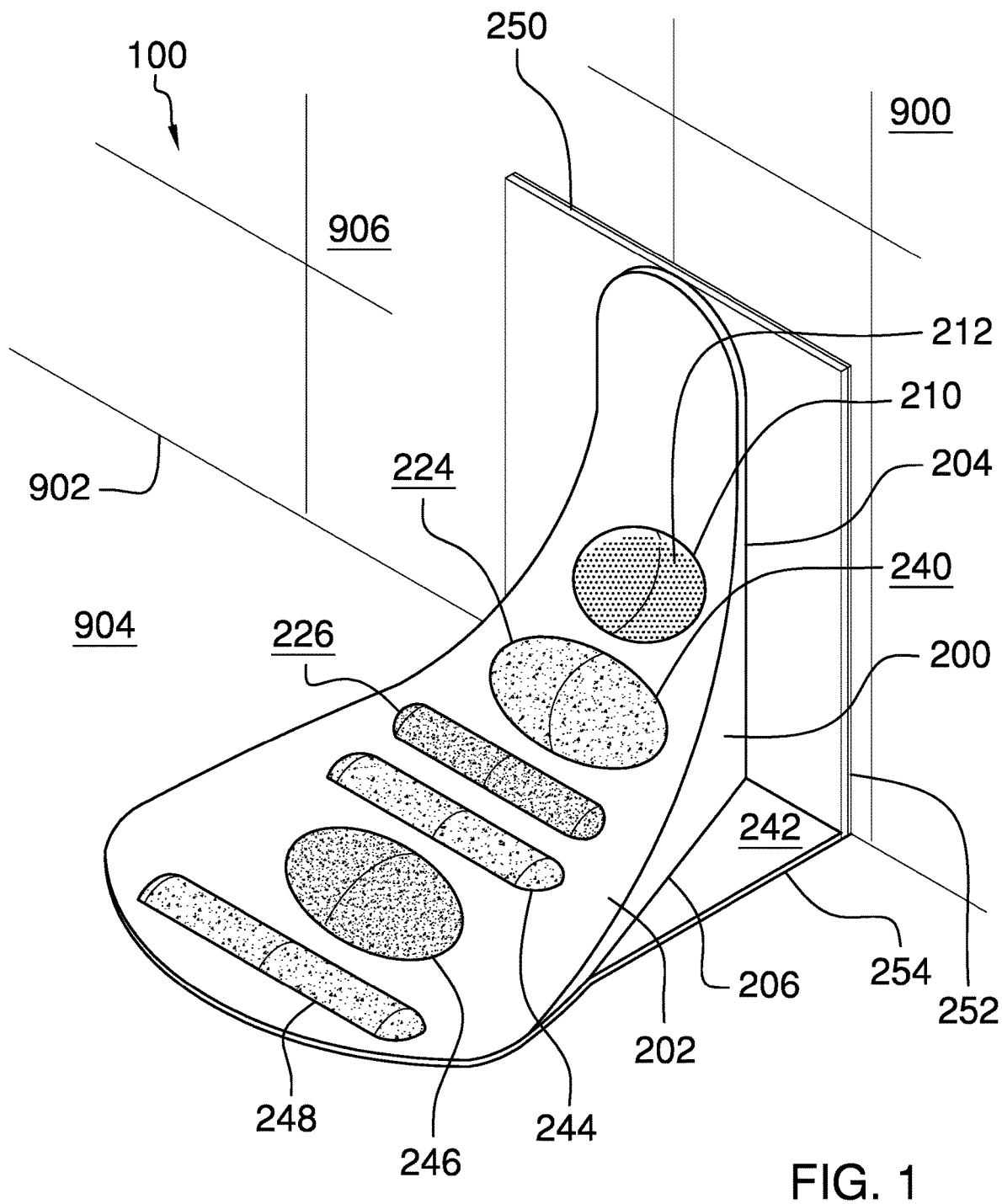
FIG. 1 is an isometric view of an embodiment of the disclosure.
Figure 2:
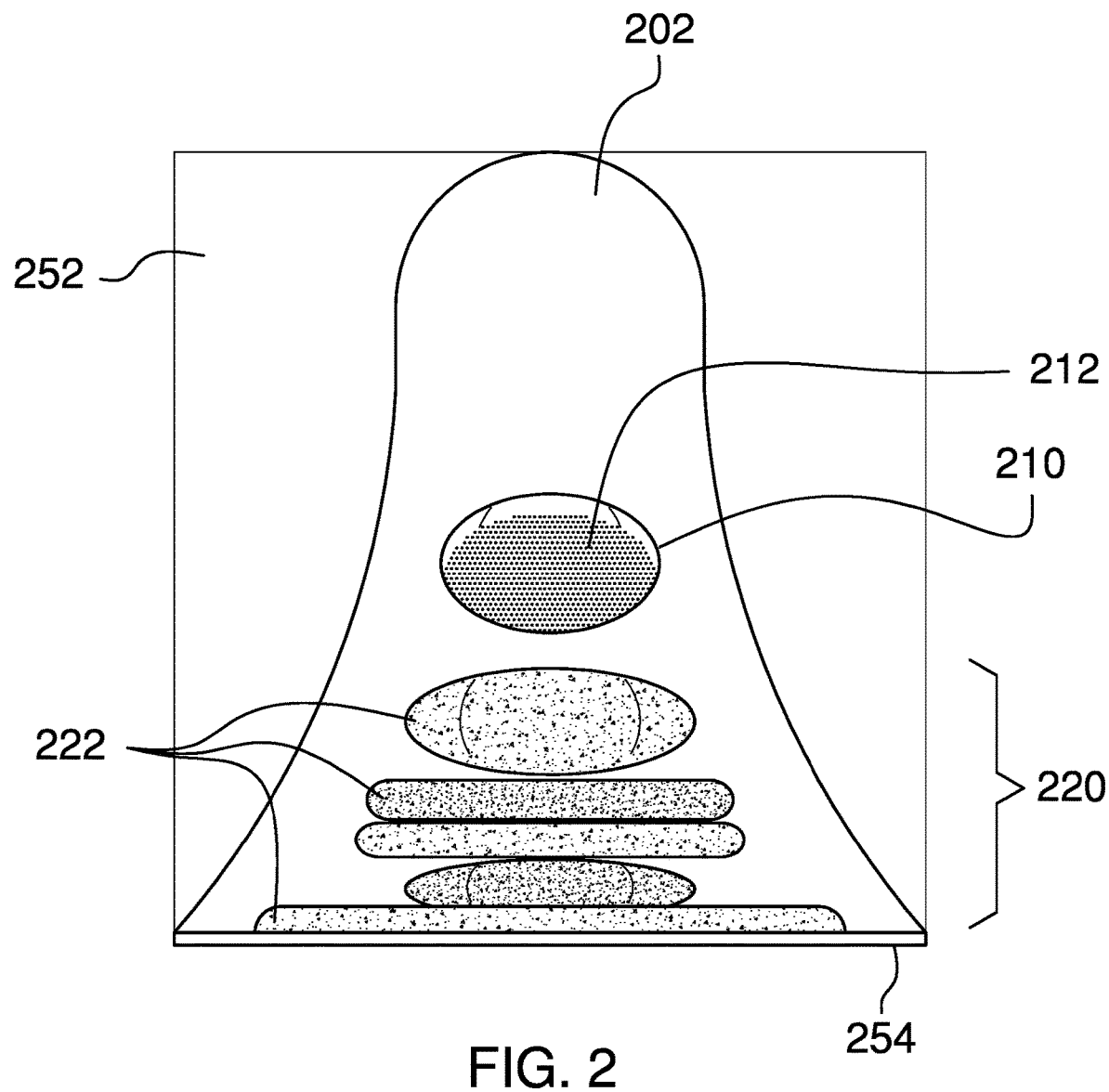
FIG. 2 is a front view of an embodiment of the disclosure.
Figure 3:
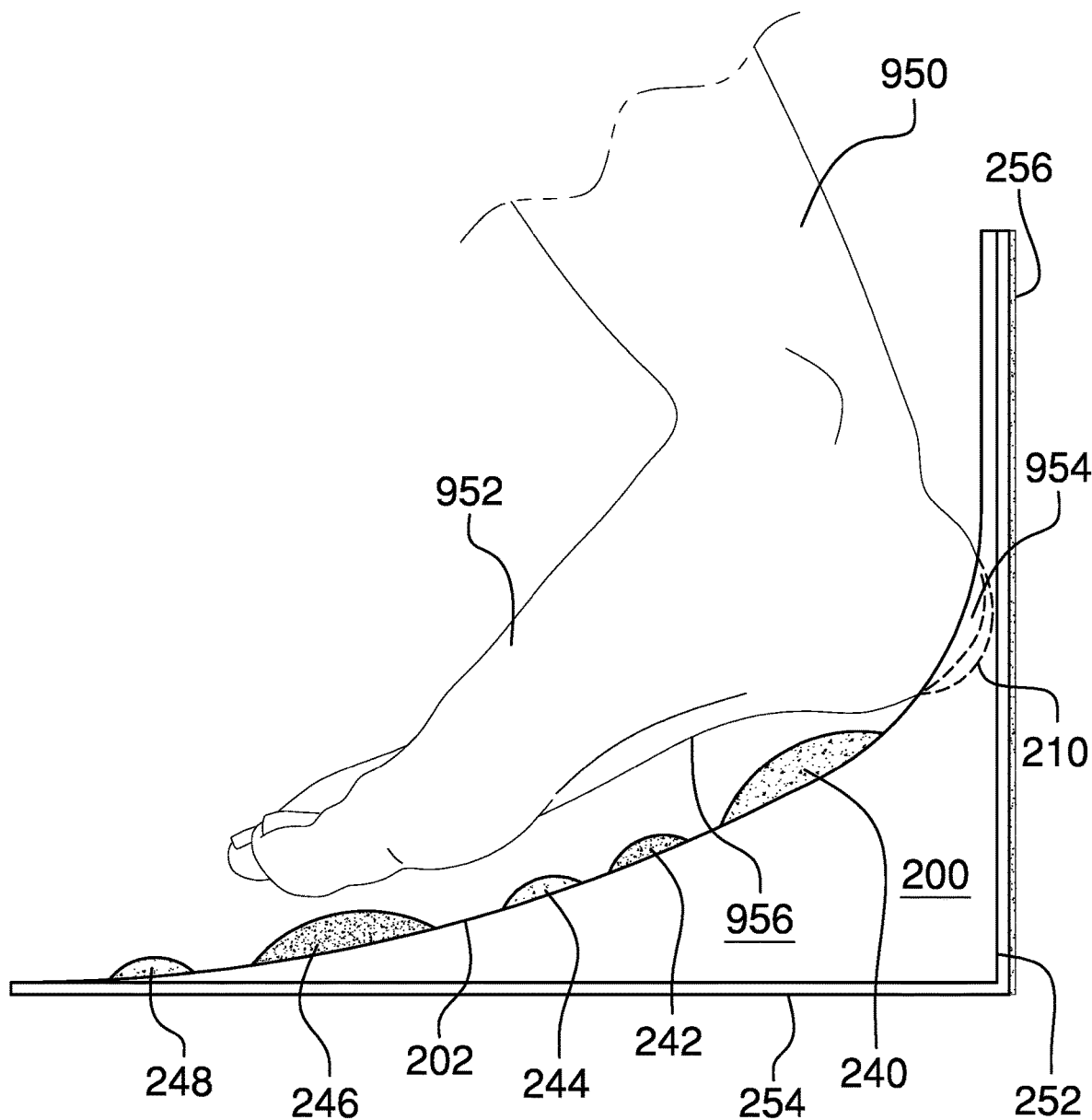
FIG. 3 is a side in-use view of an embodiment of the disclosure.
Figure 4:
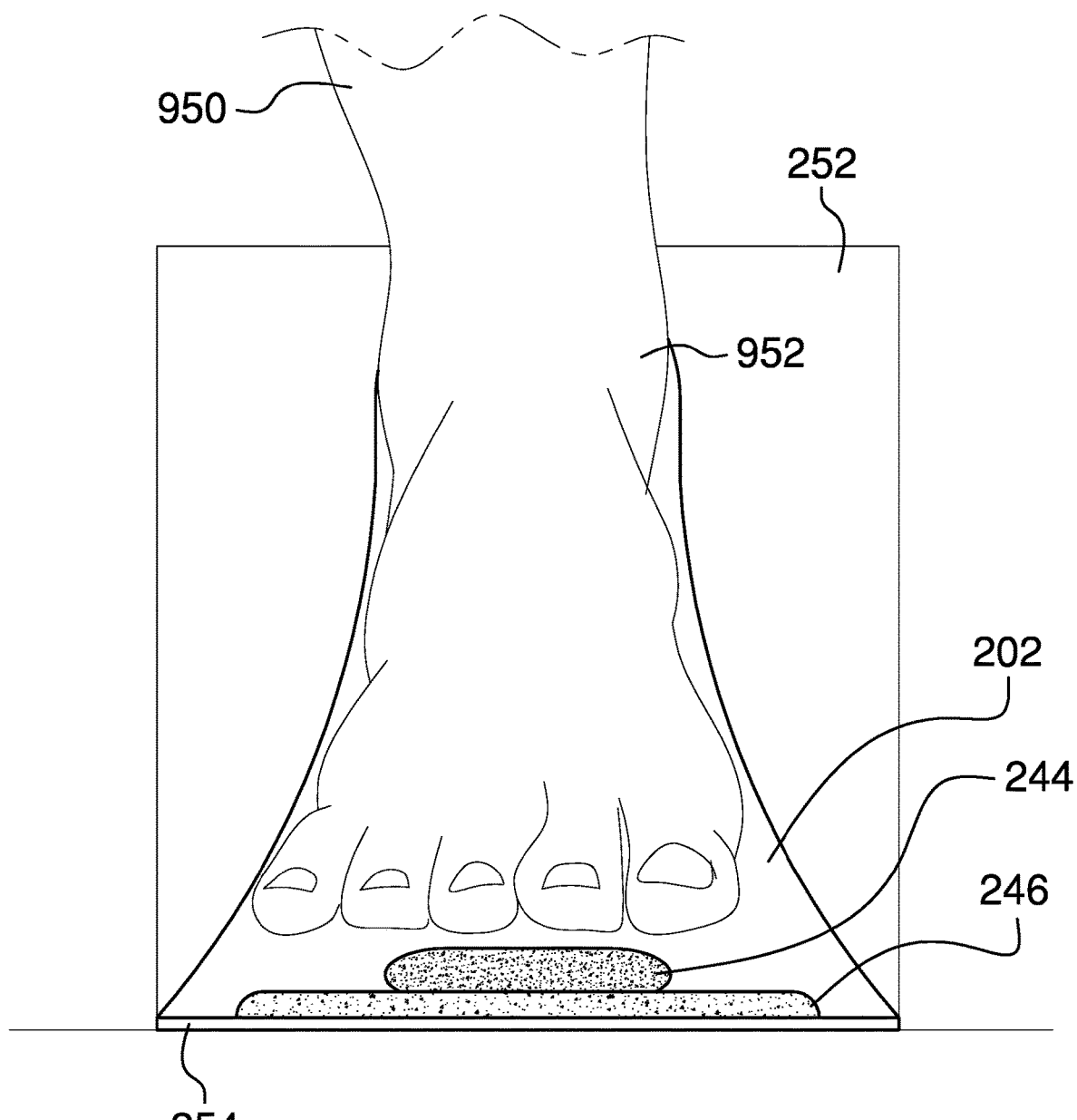
FIG. 4 is a front in-use view of an embodiment of the disclosure.

Detailed reference will now be made to a first potential embodiment of the disclosure, which is illustrated in FIGS. 1 through 4.

The foot-exfoliating device 100 (hereinafter invention) may be adapted for a user 950 to exfoliate a user's foot 952 while the user 950 is in a shower 900. The invention 100 may be mounted in a bottom corner 902 of the shower 900 where a floor meets a wall 906. The invention 100 may be adapted to exfoliate the user's foot 952 when the user's foot 952 is placed on a curved top surface 202 with a heel 954 of the user's foot pressed into a heel well 210 and when a sole 956 of the user's foot 952 is dragged along a plurality of foot scrubbers that may be accessible on the curved top surface 202. The invention 100 may comprise a scrubber body 200 and a mounting base 250. The scrubber body 200 may be operable to exfoliate. The mounting base 250 may couple the scrubber body 200 to the shower 900.

The scrubber body 200 may comprise the curved top surface 202, a flat rear surface 204, and a flat bottom surface 206. The curved top surface 202 may be adapted for the user 950 to place the user's foot 952 upon. The flat rear surface 204 may be coupled to a vertical mounting plate 252 of the mounting base 250. The flat bottom surface 206 may be coupled to a horizontal mounting plate 254 of the mounting base 250. In some embodiments, the scrubber body 200 may be made of a semi-rigid material such that the scrubber body 200 is adapted to deform slightly when the user's foot 952 presses on the scrubber body 200. The resulting deformation of the scrubber body 200 May cause the scrubber body 200 to press against different parts of the user's foot 952.

The scrubber body 200 may comprise the heel well 210. The heel well 210 may be a depression located at the upper half of the curved top surface 202. The heel well 210 may be adapted for the user 950 to place the heel 954 of the user's foot 952 into the heel well 210. The heel well 210 may comprise a heel well abrasive surface 212. The heel well abrasive surface 212 may be adapted to exfoliate the heel 954 when the heel 954 is moved within the heel well 210.

The scrubber body 200 may comprise the plurality of foot scrubbers 220. The plurality of foot scrubbers 220 may be protrusions of the scrubber body 200 that may rise above the curved top surface 202. Each of the plurality of foot scrubbers may comprise a scrubber abrasive surface 222. The plurality of foot scrubbers 220 may be adapted for the user 950 to rub the user's foot 952 against such that the scrubber abrasive surfaces may exfoliate the user's foot 952. The invention 100 may comprise at least two foot scrubbers.

The plurality of foot scrubbers 220 may comprise two different foot scrubber configurations. The two different foot scrubber configurations may be distinguished by shape. A first foot scrubber configuration 224 may comprise one half of a prolate spheroid shape divided along the major axis. A second foot scrubber configuration 226 may comprise one half of a capsule shape divided along the major axis. In common vernacular, the first foot scrubber configuration 224 may be described as the shape of one half of a football and the second foot scrubber configuration 226 may be described as the shape of one half of a hot dog.

In some embodiments, the plurality of foot scrubbers 220 may be at least two different widths, as measured laterally from end to end, and at least two different heights, as measured from the curved top surface 202 in a direction that is normal to the curved top surface 202.

In a preferred embodiment, the plurality of foot scrubbers may comprise a total of five foot scrubbers. A first foot scrubber 240 may be located adjacent the heel well 210 and May be the highest of the five foot scrubbers. The first foot scrubber 240 may be of the first foot scrubber configuration 224. A second foot scrubber 242 may be located adjacent the first foot scrubber 240 and may be lower than the first foot scrubber 240. The second foot scrubber 242 may be of the second foot scrubber configuration 226. A third foot scrubber 244 may be located adjacent the second foot scrubber 242 and may be lower than the second foot scrubber 242. The third foot scrubber may be of the second foot scrubber configuration 226. A fourth foot scrubber 246 may be located adjacent the third foot scrubber 244 and may be lower than the third foot scrubber 244. The fourth foot scrubber 246 may be of the first foot scrubber configuration 224. A fifth foot scrubber 248 may be located adjacent the fourth foot scrubber 246 and may be lower than the fourth foot scrubber 246. The fifth foot scrubber 248 may be of the second foot scrubber configuration 226.

The mounting base 250 may comprise the vertical mounting plate 252 and the horizontal mounting plate 254. The vertical mounting plate 252 may be oriented to be perpendicular to the horizontal mounting plate 254. The mounting base 250 may be coupled to the shower 900 using a waterproof adhesive 256. As a non-limiting example, the mounting base 250 may be coupled to the shower 900 using double-sided waterproof mounting tape.

Abrasive surfaces on the heel well 210 and/or the plurality of foot scrubbers 220 may result from shaping the abrasive surfaces, from applying an abrasive substance to the abrasive surfaces, or both. As non-limiting examples, the abrasive 8 surfaces selected from the heel well abrasive surface 21 and the 9 scrubber abrasive surfaces 222 may be molded as textured, non-matte surfaces. The abrasive surfaces selected from the heel well abrasive surface 21 and the scrubber abrasive surfaces 222 may be pitted, craggy, ridged, embossed, perforated, or any combination thereof. In some embodiments, the abrasive surfaces selected from the heel well abrasive surface 21 and the scrubber abrasive surfaces 222 may comprise bristles, a mesh, or any combination thereof. In some embodiments, the abrasive surfaces selected from the heel well abrasive surface 21 and the scrubber abrasive surfaces 222 may comprise pumice, charcoal, or any combination thereof.

In some embodiments, the plurality of foot scrubbers 220 may comprise at least two different coarsenesses.

In use, the invention 100 may be installed in a shower 900 by placing a waterproof adhesive 256 on the vertical mounting plate 252 and/or the horizontal mounting plate 254 of the mounting base 250 and by press the mounting base 250 into a bottom corner 902 of the shower 900 where the floor 904 meets a wall 906. While showering, the user 950 may place the user's foot 952 onto the curved top surface 202 with the heel 954 pressed into the heel well 210. The user 950 may press the heel into the heel well 210 and may move the user's foot 952 such that the heel well abrasive surface 212 exfoliates the heel 954. The user 950 may move the user's foot 952 over the plurality of foot scrubbers 220 in multiple directions such that the sole 956 of the user's foot 952 is exfoliated by one or more of the plurality of foot scrubbers 220.

Definitions

Unless otherwise stated, the words "up", "down", "top", "bottom", "upper", and "lower" should be interpreted within a gravitational framework. "Down" is the direction that gravity would pull an object. "Up" is the opposite of "down". "Bottom" is the part of an object that is down farther than any other part of the object. "Top" is the part of an object that is up farther than any other part of the object. "Upper" may refer to top and "lower" may refer to the bottom. As a non-limiting example, the upper end of a vertical shaft is the top end of the vertical shaft.

As used herein, the words "couple", "couples", "coupled" or "coupling", may refer to connecting, either directly or indirectly, and does not necessarily imply a mechanical connection.

As used herein, "front" may indicate the side of an object that is closest to a forward direction of travel under normal use of the object or the side or part of an object that normally presents itself to view or that is normally used first. "Rear" or "back" may refer to the side that is opposite the front.

As used in this disclosure, "horizontal" may be a directional term that refers to a direction that is perpendicular to the local force of gravity. Unless specifically noted in this disclosure, the horizontal direction is always perpendicular to the vertical direction.

As used in this disclosure, the word "lateral" may refer to the sides of an object or movement towards a side. Lateral directions are generally perpendicular to longitudinal directions. "Laterally" may refer to movement in a lateral direction.

As used herein, "resilient" or "semi-rigid" may refer to an object or material which will deform when a force is applied to it and which will return to its original shape when the deforming force is removed.

As used in this disclosure, "vertical" may refer to a direction that is parallel to the local force of gravity. Unless specifically noted in this disclosure, the vertical direction is always perpendicular to horizontal.

As used herein, the word "waterproof" may refer to an object that is not harmed when being exposed to water, including total submersion for a period of time. When used as a verb, "waterproof" may refer to taking steps to make an object waterproof. Non-limiting examples of such steps may include applying special coatings or using gaskets to seal seams and entry points of an enclosure.

With respect to the above description, it is to be realized that the optimum dimensional relationship for the various components of the invention described above and in FIGS. 1 through 4, include variations in size, materials, shape, form, function, and manner of operation, assembly and use, are deemed readily apparent and obvious to one skilled in the art, and all equivalent relationships to those illustrated in the drawings and described in the specification are intended to be encompassed by the invention.

It shall be noted that those skilled in the art will readily recognize numerous adaptations and modifications which can be made to the various embodiments of the present invention which will result in an improved invention, yet all of which will fall within the spirit and scope of the present invention as defined in the following claims. Accordingly, the invention is to be limited only by the scope of the following claims and their equivalents.

What is claimed is:

1. A foot-exfoliating device comprising:
a scrubber body and a mounting base;
wherein the foot-exfoliating device is adapted for a user to exfoliate a user's foot while the user is in a shower;
wherein the foot-exfoliating device is mounted in a bottom corner of the shower where a floor meets a wall;
wherein the foot-exfoliating device is adapted to exfoliate the user's foot when the user's foot is placed on a curved top surface with a heel of the user's foot pressed into a heel well and when a sole of the user's foot is dragged along a plurality of foot scrubbers that are accessible on the curved top surface;
wherein the scrubber body is operable to exfoliate;
wherein the mounting base couples the scrubber body to the shower;
wherein the scrubber body comprises the curved top surface, a flat rear surface, and a flat bottom surface;
wherein the curved top surface is adapted for the user to place the user's foot upon;
wherein the flat rear surface is coupled to a vertical mounting plate of the mounting base;
wherein the flat bottom surface is coupled to a horizontal mounting plate of the mounting base;
wherein the scrubber body comprises the plurality of foot scrubbers;
wherein the plurality of foot scrubbers are protrusions of the scrubber body that rise above the curved top surface;
wherein the plurality of foot scrubbers comprise at least two different coarsenesses.

2. The foot-exfoliating device according to claim 1
wherein the scrubber body is made of a semi-rigid material such that the scrubber body is adapted to deform when the user's foot presses on the scrubber body;
wherein the resulting deformation of the scrubber body causes the scrubber body to press against different parts of the user's foot.

3. The foot-exfoliating device according to claim 1
wherein the scrubber body comprises the heel well;
wherein the heel well is a depression located at the upper half of the curved top surface;
wherein the heel well is adapted for the user to place the heel of the user's foot into the heel well.

4. The foot-exfoliating device according to claim 3
wherein the heel well comprises a heel well abrasive surface;
wherein the heel well abrasive surface is adapted to exfoliate the heel when the heel is moved within the heel well.

5. The foot-exfoliating device according to claim 4
wherein each of the plurality of foot scrubbers comprise a scrubber abrasive surface;
wherein the plurality of foot scrubbers are adapted for the user to rub the user's foot against such that the scrubber abrasive surfaces exfoliate the user's foot.

6. The foot-exfoliating device according to claim 5
wherein the foot-exfoliating device comprises at least two foot scrubbers.

7. The foot-exfoliating device according to claim 6
wherein the plurality of foot scrubbers comprise two different foot scrubber configurations;
wherein the two different foot scrubber configurations are distinguished by shape;
wherein a first foot scrubber configuration comprises one half of a prolate spheroid shape divided along the major axis;
wherein a second foot scrubber configuration comprises one half of a capsule shape divided along the major axis.

8. The foot-exfoliating device according to claim 7
wherein the plurality of foot scrubbers are at least two different widths, as measured laterally from end to end, and at least two different heights, as measured from the curved top surface in a direction that is normal to the curved top surface.

9. The foot-exfoliating device according to claim 8
wherein the plurality of foot scrubbers comprise a total of five foot scrubbers.

10. The foot-exfoliating device according to claim 9
wherein a first foot scrubber is located adjacent the heel well and is the highest of the five foot scrubbers;
wherein the first foot scrubber is of the first foot scrubber configuration;
wherein a second foot scrubber is located adjacent the first foot scrubber and is lower than the first foot scrubber;
wherein the second foot scrubber is of the second foot scrubber configuration;
wherein a third foot scrubber is located adjacent the second foot scrubber and is lower than the second foot scrubber;
wherein the third foot scrubber is of the second foot scrubber configuration;
wherein a fourth foot scrubber is located adjacent the third foot scrubber and is lower than the third foot scrubber;
wherein the fourth foot scrubber is of the first foot scrubber configuration;

wherein a fifth foot scrubber is located adjacent the fourth foot scrubber and is lower than the fourth foot scrubber;

wherein the fifth foot scrubber is of the second foot scrubber configuration.

11. The foot-exfoliating device according to claim 8
wherein the mounting base comprises the vertical mounting plate and the horizontal mounting plate;

wherein the vertical mounting plate is oriented to be perpendicular to the horizontal mounting plate.

12. The foot-exfoliating device according to claim 11
wherein the mounting base is coupled to the shower using a waterproof adhesive.

13. The foot-exfoliating device according to claim 12
wherein the mounting base is coupled to the shower using double-sided waterproof mounting tape.

14. The foot-exfoliating device according to claim 12
wherein abrasive surfaces selected from the heel well abrasive surface and the scrubber abrasive surfaces are molded as textured, non-matte surfaces;

wherein the abrasive surfaces are pitted, craggy, ridged, embossed, perforated, or any combination thereof.

15. The foot-exfoliating device according to claim 12
wherein abrasive surfaces selected from the heel well abrasive surface and the scrubber abrasive surfaces comprises bristles, a mesh, or any combination thereof.

16. The foot-exfoliating device according to claim 12
wherein abrasive surfaces selected from the heel well abrasive surface and the scrubber abrasive surfaces comprises pumice, charcoal, or any combination thereof.

* * * * *